United States Patent [19]

Gillis

[11] Patent Number: 5,199,942
[45] Date of Patent: Apr. 6, 1993

[54] METHOD FOR IMPROVING AUTOLOGOUS TRANSPLANTATION

[75] Inventor: Steven Gillis, Mercer Island, Wash.

[73] Assignee: Immunex Corporation, Seattle, Wash.

[21] Appl. No.: 765,844

[22] Filed: Sep. 26, 1991

Related U.S. Application Data

[63] Continuation-in-part of Ser. No. 712,315, Jun. 17, 1991, abandoned.

[51] Int. Cl.$^5$ .............................................. A61M 37/00
[52] U.S. Cl. ........................................ 604/4; 604/49; 128/898; 435/240.21; 424/529; 424/85.2
[58] Field of Search ............................ 604/4-6, 604/48, 49; 128/898; 424/85.1, 85.2, 520, 529, 930, 93 V, 93 AA; 435/240.2, 240.21

[56] References Cited

U.S. PATENT DOCUMENTS

| | | | |
|---|---|---|---|
| 4,658,018 | 4/1987 | Urdal et al. | 530/351 |
| 4,690,915 | 9/1987 | Rosenberg | 514/2 |
| 4,778,879 | 10/1988 | Mertelsmann et al. | 530/351 |
| 4,863,727 | 9/1989 | Zimmerman et al. | 424/85.2 |
| 4,968,618 | 11/1990 | Young | 435/240.21 |
| 5,004,681 | 4/1991 | Boyse | 435/2 |
| 5,032,395 | 7/1991 | Clark et al. | 424/85.1 |
| 5,035,994 | 7/1991 | Civin | . |
| 5,073,627 | 12/1991 | Curtis et al. | 530/351 |
| 5,078,996 | 1/1992 | Conlon et al. | 424/85.1 |
| 5,087,571 | 2/1992 | Leder et al. | 435/240.2 |
| 5,100,378 | 3/1992 | Morgan | 604/49 |
| 5,106,733 | 4/1992 | Baker et al. | 435/69.5 |
| 5,112,757 | 5/1992 | Guguen-Guillouzo et al. | 435/240.2 |
| 5,128,259 | 7/1992 | Morgan | 435/240.2 |
| 5,135,915 | 8/1992 | Czarniecki | 514/21 |
| 5,147,784 | 9/1992 | Peault | 435/7.24 |
| 5,154,921 | 10/1992 | Sager et al. | 424/934 |

OTHER PUBLICATIONS

Moore, M. et al., "Synergy of IL-1 and GCSF: In vivo stimulation of stem-cell recovery and hematopoietic regeneration following 5-fluorouracil treatment of mice", Proc. Natl. Acad. Sci. USA, vol. 84, pp. 7134-7138, Oct. 1987.

Kalechman, Y. et al., "Protective and Restorative Role of AS101 in Combination with Chemotherapy", Cancer Research 51, 1499-1503 Mar. 1991.

Dippold, W., "Stimulation of Pancreas and Gastric Carcinoma Cell Growth by IL-3 and GM-CSF," Gastroenterology 1991; 100; 1338-1344.

(List continued on next page.)

Primary Examiner—C. Fred Rosenbaum
Assistant Examiner—Mark O. Polutta
Attorney, Agent, or Firm—Christopher L. Wight

[57] ABSTRACT

There is disclosed a method for autologous hematopoietic cell transplantation of patients receiving cytoreductive therapy, comprising: (1) obtaining hematopoietic progenitor cells from bone marrow or peripheral blood from a patient prior to cytoreductive therapy; (2) expanding the hematopoietic progenitor cells ex vivo with an ex vivo growth factor selected from the group consisting of interleukin-3 (IL-3), steel factor (SF), granulocyte macrophage-colony stimulating factor (GM-CSF), interleukin-1 (IL-1), GM-CSF/IL-3 fusion proteins and combinations thereof, to provide a cellular preparation comprising an expanded population of progenitor cells; and (3) administering the cellular preparation to the patient concurrently with or follwoing cytoreductive therapy. The inventive method optionally comprising a preliminary treatment with a recruitment growth factor to recruit hematopoietic progenitor cells into peripheral blood and a subsequent treatment with an engraftment growth factor to facilitate engraftment and proliferation of hematopoietic progenitor cells administered in the cellular preparation. The invention further provides a hematopoietic progenitor cell expansion media composition comprising cell media, an ex vivo growth factor, and autologous serum.

17 Claims, No Drawings

OTHER PUBLICATIONS

Ravagnani et al., "Role of Recombinant Human G-MCSF For Large Scale Collection of Peripheral Blood Stem Cells For Autologous Transplantation".

Molineaux et al., "Transplantation Potential of Peripheral Blood Stem Cells Induced by Granulocyte Colony Stimulating Factor" *Blood* 76:2153 (1990).

Curtis et al., "Enhanced Hematopoietic Activity of a Human Granulocyte/Macrophage Colony-Stimulating Factor-Interleukin 3 Fusion Protein" *Proc. Natl. Acad. Sci. USA* 88:5809 (1991).

Schwartz et al., "Rapid Medium Perfusion Rate Significantly Increases the Productivity and Longevity of Human Bone Marrow Cultures" *Proc. Natl. Acad. Sci. USA* 88:6760 (1991).

du Moulin et al., "Quality Assurance and Quality Control (QA/QC) in Biocare Autolymphocyte Therapy as a Model" *BioPharm* Jul./Aug. 1990, p. 30.

Siena et al., "Flow Cyotmetry for Clinical Estimation of Circulating Hematopoietic Progenitors for Autologous Transplantation in Cancer Patients" *Blood* 77:400 (1991).

McNiece et al., "Recombinant Human Stem Cell Factor Synergises with GM-CSF, G-CSF, IL-3 and Epo to Stimulate Human Progenitor Cells of the Myeloid and Erythroid Lineages" *Exp. Hematol* 19:226–231 (1991).

METHOD FOR IMPROVING AUTOLOGOUS TRANSPLANTATION

CROSS REFERENCE TO RELATED APPLICATION

The present application is a continuation-in-part of U.S. patent application Ser. No. 712,315, filed Jun. 7, 1991 now abandoned.

TECHNICAL FIELD OF THE INVENTION

The present invention relates generally to methods for autologous hematopoietic cell transplantation in patients undergoing cytoreductive therapies, and particularly to methods in which bone marrow or peripheral blood progenitor cells are removed from a patient prior to myelosuppressive cytoreductive therapy, expanded in ex vivo culture in the presence of a growth factor, and then readministered to the patient concurrent with or following cytoreductive therapy to counteract the myelosuppressive effects of such therapy. The present invention further relates to a culture media comprising one or a plurality of growth factors for expanding progenitor cells in ex vivo culture.

BACKGROUND OF THE INVENTION

Cancers are generally treated with various forms of cytoreductive therapies. Cytoreductive therapies involve administration of ionizing radiation or chemical toxins which are cytotoxic for rapidly dividing cells. Side effects of such therapy can be attributed to cytotoxic effects upon normal cells and can usually limit the use of cytoreductive therapies. A frequent side effect is myelosuppression, or damage to bone marrow cells which gives rise to white and red blood cells and platelets. As a result of myelosuppression, patients develop cytopenia which are blood cell deficits. As a result of cytopenias, patients are exposed to increased risk of infection and bleeding disorders.

Cytopenia is a major factor contributing to morbidity, mortality, and under-dosing in cancer treatment. Many clinical investigators have manipulated cytoreductive therapy dosing regimens and schedules to increase dosing for cancer therapy, while limiting damage to bone marrow. One approach involves bone marrow transplantations in which bone marrow hematopoietic progenitor cells are removed before a cytoreductive therapy and then reinfused following therapy to rescue bone marrow from toxicity resulting from the cytoreductive therapy. Progenitor cells may implant in bone marrow and differentiate into mature blood cells to supplement reduced population of mature blood cells.

High-dose chemotherapy is therapeutically beneficial because it can produce an increased frequency of objective response in patients with metastatic cancers, particularly breast cancer, when compared to standard dose therapy. This can result in extended disease-free remission for some even poor-prognosis patients. Nevertheless, high-dose chemotherapy is toxic and many resulting clinical complications are related to infections, bleeding disorders and other effects associated with prolonged periods of myelosuppression.

Currently, a human recombinant granulocyte macrophage-colony stimulating factor (GM-CSF) analog protein (sargramostim) is available in the U.S. for accelerating hematopoietic recovery following bone marrow transplantation. Sargramostim treatment has resulted in a reduction of many complications associated with bone marrow transplantation.

The existence of both marrow borne and circulating hematopoietic stem cells has been demonstrated using a variety of experimental studies and cell culture techniques. Two colony stimulating factors, GM-CSF and granulocyte colony stimulating factor (G-CSF), have been shown to increase the frequency of circulating hematopoietic progenitor or stem cells. Several studies (Gianni et al., *Lancet* 334:589 (1989); Siena et al., *Blood* 74:1905 (1989); and Molineux et al., *Blood* 76:2153 (1990)) describe in vivo administration of GM-CSF to increase the transplantation potential and frequency of primitive progenitor cells in a population of peripheral blood cells obtained from patients with tumors. These procedures represent attempts to rescue chemotherapy-induced suppresion of bone marrow by administering GM-CSF in vivo to recruit bone marrow progenitor cells into peripheral blood and then later administering harvested hematopoietic progenitor cells to patients.

More specifically, Gianni et al. describe a clinical study in which patients received high dose cyclophosphamide (7 g/m$^2$) and were transplanted with autologous peripheral blood progenitor cells and autologous bone marrow cells. Patients who were treated with GM-CSF as a progenitor cell recruitment agent, prior to harvesting peripheral blood progenitor cells, recovered more quickly from cytopenia than patients whose peripheral blood progenitor cells were not recruited by GM-CSF. Thus GM-CSF administration increased the number of peripheral blood progenitor cells. This protocol resulted in more rapid hematopoietic recovery in tested patients than in control patients who received chemotherapy without autologous bone marrow transplantation but with peripheral blood progenitor cell support.

Cancer patients treated with high dose chemotherapy and autologous bone marrow transplantation who received subsequent GM-CSF treatment have shown faster myeloid recovery than similarly treated historical controls (Brandt et al., *N. Engl. J. Med.* 318:869 (1988) and Nemunatis et al., *Blood* 72:834 (1988)). Studies have shown that the time to achieve a minimum granulocyte count of $0.5 \times 10^9/l$ after cytoreductive therapy was shorter in patients receiving GM-CSF. Granulocyte count increases were most pronounced during GM-CSF infusion. After discontinuation of GM-CSF, leukocyte counts in treated patients fell to control levels (Brandt et al., supra).

GM-CSF is also useful for autologous bone marrow transplantation following cytoreductive therapy. Socinski et al., *Lancet* 331:194 (1988) reported that GM-CSF administration after cytotoxic chemotherapy expands a circulating pool of hematopoietic progenitor cells by approximately 60-fold. Others have reported that human mononuclear cells circulating in the circulating blood, particularly during recovery from chemotherapy-induced myelosuppression, have been used to successfully reconstitute hematopoiesis after fully myeloablative (complete bone marrow toxicity) treatments (See, e.g., Bell et al., *Hematol, Oncol.*5:45 (1987)).

Mason et al., *Proc. Amer. Assoc. Cancer Res.* 32:193 (1991), reported that in vitro interleukin-3 (IL-3) alone or in combination with interleukin-6 (IL-6) increased the number of colony forming progenitors from human blood progenitor cells two fold in vitro. Mason et al. also reported that GM-CSF did not expand the colony forming progenitor population in vitro. Accordingly, autologous hematopoietic cell transplantation has proven to be a valuable technique to speed recovery from cytoreductive therapies. Improvements in autologous hematopoietic cell transplantation can further speed recovery from cytoreductive therapies and even allow the use of higher and more effective doses in cytoreductive therapies. This invention provides an improvement in autologous hematopoietic cell transplantation.

SUMMARY OF THE INVENTION

The invention is a method for conducting autologous progenitor cell transplantation, comprising: (1) obtaining hematopoietic progenitor cells from a patient prior to cytoreductive therapy; (2) expanding the hematopoietic progenitor cells ex vivo with an ex vivo growth factor selected from the group consisting of granulocyte macrophage-colony stimulating factor (GM-CSF), interleukin-3 (IL-3), steel factor (SF), GM-CSF/IL-3 fusion proteins, and combinations thereof, to provide a cellular preparation comprising increased numbers of hematopoietic progenitor cells; and (3) administering the cellular preparation to the patient in conjunction with or following cytoreductive therapy. Interleukin-1 (IL-1α or IL-1β) can also be used as an ex vivo growth factor when used together with at least one other growth factor. Progenitor cells may be obtained from peripheral blood harvest or bone marrow explants.

The inventive method optionally comprises a preliminary in vivo procedure comprising administering a recruitment growth factor to the patient to recruit hematopoietic progenitor cells into peripheral blood prior to their harvest, wherein the recruitment growth factor is selected from the group consisting of GM-CSF, SF, G-CSF, IL-3, GM-CSF/IL-3 fusion proteins, and combinations thereof.

The inventive method optionally comprises a subsequent in vivo procedure comprising administering an engraftment growth factor to the patient following autologous transplantation of the cellular preparation to facilitate engraftment and augment proliferation of engrafted hematopoietic progenitor cells from the cellular preparation. The engraftment growth factor is selected from the group consisting of GM-CSF, IL-3, SF, GM-CSF/IL-3 fusion proteins and combinations thereof.

The present invention further includes a progenitor cell expansion media comprising cell growth media, autologous serum, and a growth factor selected from the group consisting of SF, IL-1, IL-3, GM-CSF, GM-CSF/IL-3 fusion proteins, and combinations thereof with the proviso that IL-1 must be used in combination with at least one other growth factor.

DETAILED DESCRIPTION OF THE INVENTION

Growth factors can be used in vivo to induce hematopoietic progenitor cells in bone marrow to proliferate and to mobilize such hematopoietic progenitor cells into peripheral blood. Hematopoietic progenitor cells harvested from peripheral blood can be used for hematopoietic rescue therapy of patients treated with cytoreductive agents. The present invention involves ex vivo treatment of hematopoietic progenitor cells from peripheral blood or bone marrow with growth factors to increase their numbers prior to infusion or transplantation. In addition, growth factors can be used to facilitate engraftment and proliferation of transplanted hematopoietic progenitor cells following transplantation. Hematopoietic reconstitution of a patient undergoing cytoreductive therapy can reduce the incidence of infection and bleeding complications of patients treated with high doses of cytoreductive therapies, such as myelosuppressive cancer chemotherapeutic agents or high doses of radiotherapy.

The present invention involves ex vivo and/or in vivo administration of growth factors in connection with autologous bone marrow or peripheral blood progenitor cell transplantation. The ex vivo growth factor, recruitment growth factor and engraftment growth factor are selected from the group consisting of GM-CSF, IL-3, SF, IL-1, GM-CSF/IL-3 fusion proteins, and combinations thereof. Of the foregoing, a combination of SF and a GM-CSF/IL-3 fusion protein is preferred for the ex vivo growth factor. Moreover, IL-1 (comprising IL-1α or IL-1β) should be administered in combination with at least one other growth factor and preferably as an ex vivo growth factor.

Granulocyte macrophage-colony stimulating factor (GM-CSF) is commercially and clinically available as an analog polypeptide (Leu$^{23}$) under the trademark LEUKINE®. The generic name for recombinant human Leu$^{23}$ GM-CSF analog protein expressed in yeast is Sargramostim. Cloning and expression of native sequence human GM-CSF was described in Cantrell et al., *Proc. Natl. Acad. Sci. U.S.A* 82:6250 (1985).

Interleukin-3 (IL-3) occurs in two major allelic variations. The predominant human allele encodes an IL-3 molecule having a proline residue at position 8 of the mature polypeptide which is described in WO88/04691 published on Jun. 30, 1988, and in U.S. patent application Ser. No. 07/004,466, filed on Jan. 20, 1987, the disclosure of which is incorporated by reference herein. The other IL-3 allele has a serine residue at position 8 of the mature polypeptide.

Steel factor (SF) has also been called mast cell growth factor (MGF), stem cell factor (SCF), and Kit Ligand (KL). All of the names for this factor refer to the ligand for the c kit proto-oncogene. SF has been described in a series of seven papers in the Oct. 5, 1990 issue of Cell (Williams et al., *Cell* 63:167, 1990; Copeland et al., *Cell* 63:175, 1990; Flanagan and Leder, *Cell* 63:185, 1990; Zsebo et al., *Cell* 63:195, 1990; Martin et al., *Cell* 63:203, 1990; Zsebo et al., *Cell* 63:213, 1990; Huang et al., *Cell* 63:225, 1990; and Anderson et al., *Cell* 63:235, 1990). Expression of various recombinant forms of SF has been described in U.S. patent application Ser. No. 07/586,073, filed Sep. 21, 1990 and U.S. patent application Ser. No. 07/713,715 filed Jun. 12, 1991, the disclosures of which are incorporated by reference herein. SF has been found to stimulate proliferation and recruitment of early myeloid and lymphoid lineage progenitor cells and possibly even the most primitive hematopoietic stem cells.

Interleukin-1 has been found to exist in two forms, IL-1α and IL-1β (March et al., *Nature* 315:641, 1985). Both IL-1α and IL-1β bind to IL-1 receptors (Type I and Type II) to transduce signal. IL-1α is active in both precursor and mature forms, whereas IL-1β is only active in mature form but not in a precursor form (March et al., supra). IL-1 also include active fragments and analogs with altered amino acid sequences and derivatives, such as fusion proteins having an IL-1 component and IL-1 biological activity (Mosley et al., *Proc. Natl. Acad. Sci.*, USA 84:4572, 1987).

Fusion protein comprising GM-CSF and IL-3 components are described in U.S. patent application Ser.

No. 07/567,983 filed Oct. 14, 1990, the disclosure of which is incorporated by reference herein. A particular GM-CSF/IL-3 fusion protein (PIXY321) has been found to interact with GM-CSF receptors and/or IL-3 receptors (Curtis et al., *Proc. Natl. Acad. Sci. USA* 88:5809, 1991). PIXY321 is a GM-CSF/IL-3 fusion protein having Leu$^{23}$ Asp$^{27}$ Glu$^{34}$ hGM-CSF/Gly$_4$ Ser Gly$_5$ Ser/Pro$^8$ Asp$^{15}$ Asp$^{70}$ hIL-3. Thus, this protein comprises a triply-substituted GM-CSF domain fused to a doubly-substituted Pro$^8$ IL-3 domain via a linker or spacer domain comprising glycine and serine residues. Preferably, hematopoietic progenitor cells are expanded ex vivo using an effective amount of a growth factor comprising a combination of SF and a GM-CSF/IL-3 fusion protein (such as PIXY321).

The growth factors used in the methods of the present invention are polypeptides. If recruitment or engraftment growth factors are employed, normal routes of in vivo polypeptide administration are preferred, including subcutaneous, intravenous (iv), intraperitoneal (ip), intramuscular (im), and intralymphatic (il). Most preferably in vivo administration of a growth factor is subcutaneous.

Ex vivo use of a growth factor is by direct addition to cultures of hematopoietic progenitor cells from peripheral blood or bone marrow in physiological buffer or culture medium. Preferred progenitor cell expansion medium is, for example, minimal essential medium supplemented with autologous serum and antibiotics. Progenitor cell expansion media, according to the present invention, comprises one or a plurality of ex vivo growth factors in culture medium, such as minimal essential medium supplemented with autologous serum and possibly antibiotics. Other culture media include, for example, Hanks, McCoys, RPMI 1640 minimal essential media (MEM) and others, and include from 1% to 20% autologous serum and possibly antibiotics.

Preferred in vivo dosages of recruitment or engraftment growth factors are from about 10 $\mu$g/kg/day to about 800 $\mu$g/kg/day for SF; from about 1 $\mu$g/kg/day to about 100 $\mu$g/kg/day for GM-CSF and for IL-3; and from about 1 $\mu$g/kg/day to about 100 $\mu$g/kg/day for GM-CSF/IL-3 fusion proteins. Preferred ex vivo growth factor concentrations in progenitor cell expansion media are from about 1 ng/ml to about 10 $\mu$g/ml for SF, and from about 10 ng/ml to about 200 $\mu$g/ml for GM-CSF, IL-3, IL-1 and GM-CSF/IL-3 fusion proteins.

Progenitor cells may be obtained from human mononuclear cells obtained from bone marrow and peripheral blood. Progenitor cells may be separated from peripheral blood, for example, by density gradient centrifugation such as a Ficoll Hypaque ® system. Another means for separating hematopoietic progenitor cells obtained from bone marrow or peripheral blood involves separating with antibodies that recognize a stage-specific antigen on immature human hematopoietic progenitor cells. One example of an antibody recognition method for separating human hematopoietic progenitor cells is described in Civin, U.S. Pat. No. 5,035,994 the disclosure of which is incorporated by reference herein.

Once hematopoietic progenitor cells are obtained by a particular separation technique, they may be stored in cryogenic conditions or expanded ex vivo according to the present invention. Stored cells may later be rapidly thawed and expanded ex vivo according to the present invention.

Hematopoietic progenitor cells treated ex vivo with growth factors are readministered to patients by autologous transplantation. Cells are cultured ex vivo in the presence of a growth factor for at least one day and no more than two weeks. Cells can be stored and retain viability either prior to expansion with growth factor or after expansion with growth factor. Cell storage is preferably under cryogenic conditions such as liquid nitrogen. Cultured cells are washed before being administered to the patient. Expanded cells are administered following completion of cytoreductive therapy or up to 72 hours after completion of cytoreductive therapy. Cell administration usually is by infusion over 2 to 5 days. Preferably, from about $10^7$ to about $10^9$ expanded mononuclear cells/kg (approximately $10^5$ expanded progenitor cells/kg) are administered to the patient for an autologous transplantation.

Preferably, the hematopoietic progenitor cells are cultured ex vivo for approximately one week. Preferably, the growth factor is a combination of SF and a GM-CSF/IL-3 fusion protein. Most preferably, the GM-CSF/IL-3 fusion protein is PIXY321. Preferably, the recruitment growth factor and the engraftment growth factor is a combination of SF and a GM-CSF/IL-3 fusion protein.

In a preferred embodiment, the method of the present invention comprises in vivo treatment of the patient prior to cytoreductive therapy (after recovery from any previous cytoreductive therapy) with a recruitment growth factor, ex vivo expansion of hematopoietic progenitor cells (obtained from the patient's peripheral blood and/or bone marrow) with a combination of a GM-CSF/IL-3 fusion protein and SF, and in vivo treatment of the patient with an engraftment growth factor after administration of the cellular preparation (ex vivo treated hematopoietic progenitor cells). In vivo administration of a recruitment growth factor helps to stimulate proliferation of more primitive hematopoietic progenitor cells in bone marrow and to recruit hematopoietic progenitor cells into peripheral blood. Peripheral blood progenitor cells and/or bone marrow cells are expanded and later used for hematopoietic rescue following cytoreductive therapy. The patient may be treated with an engraftment growth factor beginning one to three days following the last administration of the cellular preparation. The engraftment growth factor facilitates engraftment and proliferation of hematopoietic progenitor cells. Hematopoietic rescue helps reduce patient morbidity associated with myelosuppressive or myeloablative cytoreductive therapy protocols as manifest in decreased infections, susceptibility to infections and bleeding disorders.

Hematopoietic progenitor cells obtained from human peripheral blood from normal volunteers were expanded ex vivo by culturing in progenitor cell expansion media comprising selected single growth factors or combinations of growth factors. Culturing hematopoietic progenitor cells ex vivo in the presence of selected growth factors resulted in expansion of myeloid lineage and erythroid lineages progenitor cells as determined by colony assays for myeloid (GM-CSF) and erythroid (BFU-e) components. Example 1 herein presents data from a series of experiments utilizing hematopoietic progenitor cells cultured in different progenitor expansion media. Data presented in Example 1 demonstrate increases in expansion indeces of myeloid and erythroid components. Progenitor cell expansion media comprising PIXY321, IL-3 or SF growth factors was able to expand myeloid and erythroid progenitor cell populations to a greater extent than media without added growth factor. Media comprising a combination of SF and PIXY321 consistently produced myeloid and erythroid progenitor cell expansion greater than media coprising SF alone, PIXY321 alone, IL-1α alone, G-CSF alone, IL-3 alone or even the combination of SF and IL-3 or G-CSF and SF. Another particularly effective growth factor combination was IL-1α and PIXY321 for both myeloid and erythroid prenitor cell expansion however, this combination did not maintain high numbers of myeloid progenitor cells. Accordingly, the claimed method for expanding hematopoietic progenitor cells in vitro with an ex vivo growth factor or combination of growth factors can improve expansion of at least myeloid and erythroid lineage populations of hematopoietic progenitor cells obtained from human peripheral blood. Moreover, the growth factor combination of PIXY321 and SF was particularly effective.

The present invention comprises ex vivo treatment of hematopoietic progenitor cells from peripheral blood or bone marrow with a growth factor. The growth factor is selected from the group consisting of GM-CSF, IL-3, SF, IL-1, GM-CSF/IL-3 fusion proteins and combinations thereof. Ex vivo progenitor cell expansion in media containing a growth factor is capable of expanding the number of hematopoietic progenitor cells originally harvested from peripheral blood or bone marrow and improves the ability of the expanded population of progenitor cells to engraft and proliferate in bone marrow and other hematopoietic tissue when later administered in an autologous transplantation.

This ability to significantly expand a population of hematopoietic progenitor cells for autologous transplantation provides an improved autologous hematopoietic cell transplantation technique to allow for high doses or more intensive cytoreduction therapies. Ex vivo treatment with the growth factor improves hematopoietic rescue of the patient following myeloablative or myelosuppressive cytoreductive therapy regimens. Treatment of hematopoietic progenitor cells obtained from peripheral blood or bone marrow further allows for higher dosing of cytoreductive therapeutic agents while reducing the risk of infection and bleeding disorders to the patient.

Therefore, the method of hematopoietic rescue by autologous transplantation, according to the present invention, helps to reduce morbidity (infection and bleeding disorders) and myelotoxicity (bone marrow toxicity) associated with higher doses of cytoreductive therapy and constitutes an improvement over current autologous hematopoietic cell transplantation techniques. The following examples illustrate in vitro data of hematopoietic progenitor cell expansion and various clinical therapeutic procedures for hematopoietic rescue and autologous hematopoietic cell transplantation.

EXAMPLE 1

This example illustrates a comparison of expansion ratios for human hematopoietic progenitor cells expanded ex vivo with progenitor expansion media comprising different growth factors or growth factor combinations or media without added growth factor in a series of experiments. The human hematopoietic progenitor cells were obtained from peripheral blood of normal volunteers.

Human peripheral blood was obtained from normal, healthy, volunteers via veinipuncture and collected in a heparinized tube. Progenitor cells were obtained from peripheral blood by density gradient centrifugation on Histopaque ® (Sigma, St. Louis) and a mononuclear layer of cells were obtained. The mononuclear cells, containing a population of human hematopoietic progenitor cells were washed twice in phosphate buffered saline (PBS) and viable cells counted by trypan blue due exclusion.

Ex vivo cultures were made from approximately $10^7$ viable cells in 10 ml of Super McCoys medium supplemented with 20% fetal bovine serum. It should be noted that fetal bovine serum was substituted for autologous serum in this experiment because the cells expanded in this experiment would not be readministered to their original donors. Cells were cultured and expanded in petri dishes incubated at 37° C. in an atmosphere of 7% $CO_2$, 8% $O_2$, 85% air. Culture media were replaced on day 4 with new growth factor(s).

Growth factors were added to media at concentrations according to Table 1:

TABLE 1

| Growth Factor | Concentration |
| --- | --- |
| PIXY321 | 100 ng/ml |
| SF | 1 µg/ml |
| IL-3 | 100 ng/ml |
| IL-1α | 100 ng/ml |
| G-CSF | 100 ng/ml |

Progenitor cells in culture tend to be nonadherent. For each colony assay, 50% of nonadherent cells in each culture were obtained. Cells were separated from media by centrifugation, washed twice and viable cells counted by trypan blue due exclusion.

Two colony assays were performed. A GM-CFU assay (Lu et al., Exp. Hematol. 13:989, 1985) measured a myeloid component of the progenitor cell population and BFU-e assay (Lu et al., supra) measured an erythroid component. Viable cells were plated in a methyl cellulose cloning media (Terry Fox Labs, Vancouver, B.C.) in the presence of PIXY321 (GM-CFU) or PIXY321 plus erythropoietin (BFU-e). The number of myeloid or erythroid colonies were counted and this number was divided by the number of cells plated into each well to determine a colony-forming capacity (CFC) incidence. CFC incidence was multiplied by total cell number to determine CFC number per culture. Each CFC number was compared to a day 0 CFC number to determine an expansion ratio for each progenitor expansion media tested.

Myeloid and erythroid component cell expansion was determined after 4 and 8 days of incubation. An expansion number of 1 means that there was no expansion of colony number, whereas an expansion number of 2 means that the number of colonies doubled from the day 0 number.

A first experiment compared myeloid and erythroid expansion of hematopoietic progenitor cells cultured and expanded hematopoietic progenitor cell expansion media comprising McCoys media plus 20% FCS and supplemented with PIXY321, SF or a combination of PIXY321 and SF.

TABLE 2

| Growth Factor | Day 4 | | Day 8 | |
| --- | --- | --- | --- | --- |
| | GM-CFU | BFU-e | GM-CFU | BFU-e |
| Media only | 0.58 | 0.74 | 0.63 | 0.89 |
| PIXY321 | 1.41 | 2.19 | 4.29 | 13.63 |
| SF | 1.59 | 0.76 | 2.49 | 4.89 |

TABLE 2-continued

| Growth Factor | Day 4 | | Day 8 | |
|---|---|---|---|---|
| | GM-CFU | BFU-e | GM-CFU | BFU-e |
| PIXY321 + SF | 3.77 | 8.33 | 12.68 | 22.65 |

Data from the first experiment show that both PIXY321 and SF improved myeloid and erythroid progenitor cell expansion. The combination of PIXY321 and SF showed a more-than-additive expansion of myeloid erythroid cells.

A second experiment compared myeloid and erythroid progenitor cell expansion when hematopoietic progenitor cells were cultured in the presence of PIXY321, SF and IL-1α. In this experiment, the concentration of mononuclear cells added to media was decreased from $10^6$ cells/ml in the first experiment to $4 \times 10^5$ cells/ml in this experiment.

TABLE 3

| Growth Factor | Day 4 | | Day 8 |
|---|---|---|---|
| | GM-CFU | BFU-e | GM-CFU |
| Media | 0.875 | 0.32 | 3.50 |
| IL-1α | 0.74 | 0.21 | 1.80 |
| SF | 1.375 | 0.42 | 4.26 |
| PIXY321 | 2.70 | 1.90 | 19.01 |
| IL-1α + SF | 1.50 | 0.80 | 2.11 |
| IL-1α + PIXY321 | 8.17 | 3.12 | 5.84 |
| SF + PIXY321 | 7.31 | 4.43 | 32.64 |
| SF + PIXY321 + IL-1α | 5.40 | 4.95 | 5.25 |

The data from the second experiment show expansion of myeloid and erythroid lineage progenitor cells when expanded with PIXY321 alone as a growth factor but not with either SF alone or IL-1α alone as growth factors. Growth factor combinations IL-1α+PIXY321, SF+PIXY321, and SF+PIXY321+IL-1α provided striking expansions in both myeloid and erythroid lineage progenitor cell numbers on day 4, however the day 8 results showed improvement only for SF+PIXY321 and for PIXY321 alone.

A third experiment compared myeloid progenitor cell expansion on days 4 and 8 for cultures containing growth factors PIXY321, SF, IL-3 and combinations.

TABLE 4

| Growth Factor | Day 4 GM-CFU | Day 8 GM-CFU |
|---|---|---|
| Media | 0.50 | 0.74 |
| PIXY321 | 2.18 | 4.83 |
| SF | 1.25 | 1.08 |
| IL-3 | 1.99 | 3.60 |
| PIXY321 + SF | 4.01 | 7.05 |
| IL-3 + SF | 2.65 | 4.22 |

These data show that a growth factor combination of PIXY321 and SF provide greater myeloid progenitor cell expansion than a growth factor combination of IL-3 and SF.

A fourth experiment compared myeloid progenitor cell expansion on days 4 and 8 for cultures containing growth factors PIXY321, SF, G-CSF and combinations. The concentration of mononuclear cells added to media was $10^6$ cells/ml.

TABLE 5

| Growth Factor | Day 4 GM-CFU | Day 8 GM-CFU |
|---|---|---|
| Media | 0.76 | 0.80 |
| PIXY321 | 2.69 | 3.94 |
| SF | 1.84 | 0.76 |
| G-CSF | 0.96 | 1.42 |
| PIXY321 + SF | NA | 3.56 |
| PIXY321 + G-CSF | 5.02 | 12.50 |
| SF + G-CSF | 3.36 | 1.79 |
| PIXY321 + SF + G-CSF | 6.34 | 3.57 |

NA indicates that there were problems with the assay.

These data show that combinations with G-CSF were not as effective as the combination of PIXY321 and SF.

A summary of the four experiments confirms the utility of addition of a growth factor or a combination of growth factors to media to increase expansion of progenitor cells cultured ex vivo.

EXAMPLE 2

This example illustrates a clinical protocol providing myeloablative chemotherapy and peripheral blood progenitor cell expansion according to the present invention. The clinical protocol is designed to evaluate the effectiveness of hematopoietic reconstitution of bone marrow with peripheral blood derived (and GM-CSF recruited) hematopoietic progenitor cells that are expanded ex vivo with with a growth factor combination of SF and PIXY321.

After full recovery from any previous cycle of chemotherapy (leukocyte count of greater than 3000/mm$^3$ and platelet count of greater than 100,000/mm$^3$) GM-CSF (Sargramostim) bid is administered sc, at a dose of 5 mcg/kg/day. On days 6, 8 and 9 of GM-CSF recruitment growth factor, peripheral blood is collected. Leukophoresis is performed using a 9 liter, 3 hour treatment with collection from set to obtain a preferential mononuclear cell collection from peripheral blood to form the population of hematopoietic progenitor cells. Cell counts of greater than $2 \times 10^8$/kg are normally obtained from each peripheral blood collection. Autologous serum is also obtained from each patient to use in a progenitor cell expansion media.

Hematopoietic progenitor cells obtained from peripheral blood and subject to leukophoresis are assayed for colony forming activity (CFU-GM, CFU-GEMM, BFU-e and Blast Cell) and phenotyped for CD34, CD33 and CD7. Ex vivo cultures are started with cell concentration of about $5 \times 10^5$ mononuclear cells/ml in McCoys medium supplemented with 10% autologous serum, 100 ng/ml SF and 100 ng/ml PIXY321. Cells are cultured for 12 days with media changes on days 4 and 8. Cells are evaluated thrice weekly for cell counts, differential, progenitor cell capability and phenotype. After 12 days of expansion, nonadherent cells are harvested, washed to remove growth factor and cryopreserved in autologous serum in liquid nitrogen at a concentration range of $10^5$ to $2 \times 10^7$ cells/ml.

Each patient undergoes a high dose, myeloablative chemotherapy protocol comprising cyclophosphamide (1875 mg/m$^2$) infused over 1 hour on each of three successive days, cis-diaminodichloroplatinum (55 mg/m$^2$/day) infused continuously over three days (total dose 165 mg/m$^2$ over 72 hours) and BCNU on the last day of cytoreductive therapy at 600 mg/m$^2$ infused at a rate of 5 mg/m$^2$/min.

Two days after the last day of high dose myeloablative chemotherapy, each patient is administered his or her expanded progenitor cells. The cells are thawed rapidly and infused iv at a rate of 10 cc/min of $10^6$ cells/ml. The cells are administered in equal aliquots on each of three successive days.

Beginning about three hours after the last cell infusion, GM-CSF is administered (iv or sc) at a dose of 12 mcg/kg/day for a total of 7 days. GM/CSF is further administered for another 14 days at a dose of 6 mcg/kg/day (iv or sc).

This procedure combines the antitumor benefits of myeloablative high dose chemotherapy with the ability of the present inventive method to expand hematopoietic progenitor to improve bone marrow, hematopoietic and immunologic rescue of patients.

EXAMPLE 3

This example illustrates a patient treatment schedule with autologous transplantation for hematopoietic rescue of myelotoxicity when myelotoxicity is caused by treatment with a group of cytoreductive cancer chemotherapeutic agents causing myeloreduction but not myeloablative results. Patients with solid tumors, such as small cell lung carcinoma (SCLC), colon carcinoma, or melanoma are pre-treated for one to seven days with SF at a dose of 100–4000 $\mu g/m^2$/day, and PIXY321 at a dose of 5–250 $\mu g/m^2$/day. After pre-treatment, peripheral blood is collected and hematopoietic progenitor cells are isolated by a leukophoresis technique, such as one described in Kessinger et al., *Blood* 74:1260, 1989.

The progenitor cells are cultured and expanded for 7–14 days in McCoys medium, 10% autologous serum, SF at 1 $\mu m$/ml and PIXY321 at 100 ng/ml. Media is changed every 4 days. During culturing of the peripheral blood-derived progenitor cells, patients undergo cytoreductive therapy at doses up to 50% higher than could otherwise be tolerated in the absence of hematopoietic rescue.

After completion of cell expansion, cultured progenitor cells are washed to remove culture medium and growth factors and suspended in buffered saline. Supplemented with autologous serum, expanded progenitor cells are reinfused to the same patient (autologous transplantation) to effect a hematopoietic rescue from high dose cytoreductive chemotherapy.

EXAMPLE 4

This example illustrates a patient treatment schedule with autologous transplantation for hematopoietic rescue of myelotoxicity caused by cytoreductive treatment. Patients are pre-treated for 1–7 days with GM-CSF at a dose of 50–3000 $\mu g/m^2$/day. After pretreatment, both peripheral blood and bone marrow are collected and hematopoietic progenitor cells are isolated. The isolated progenitor cells are cultured with SF and PIXY-321 as described in Example 3. Patients under cytoreductive therapy and the cultured hematopoietic progenitor cells are readministered in an autologous transplantation.

EXAMPLE 5

This example illustrates another patient treatment schedule with autologous transplantation for hematopoietic rescue of myelotoxicity caused by cytoreductive cancer therapy agents. The patient treatment schedule follows the schedule of Example 3, except bone marrow is removed instead of peripheral blood progenitor cells.

EXAMPLE 6

This example illustrates another patient treatment schedule with autologous transplantation for hematopoietic rescue of myelotoxicity caused by cytoreductive cancer therapy agents. The patient treatment schedule follows the schedule of Example 4 except only bone marrow is removed instead of both bone marrow and peripheral blood progenitor cells.

EXAMPLE 7

This example illustrates another patient treatment schedule with autologous transplantation for hematopoietic rescue of myelotoxicity caused by cytoreductive cancer therapy agents. The patient treatment schedule follows the schedule of Example 3, except both bone marrow and peripheral blood progenitor cells are removed, instead of only peripheral blood progenitor cells.

EXAMPLE 8

This example illustrates a patient treatment schedule with autologous transplantation of ex vivo stimulated hematopoietic progenitor cells followed by subsequent in vivo administration of an engraftment growth factor to improve implantation and proliferation of hematopoietic progenitor cells. Patients with solid tumors are pretreated for seven days with GM-CSF (10 $\mu g$/kg/day) or PIXY321 (10 $\mu g$/kg/day). Peripheral blood (two pints) or bone marrow is removed. Hematopoietic progenitor cells are separated by density gradient centrifugation using standard techniques. Separated mononuclear cells are cultured in minimum essential media supplemented with 10% autologous serum, pyruvate, penicillin-streptomycin-glutamine and growth factor (100 ng/ml SF and 100 ng/ml PIXY-321) to form a culture of expanded hematopoietic progenitor cells. The cells are cultured in a humidified atmosphere (5% $CO_2$) at a density between $0.1 \times 10^5$ and $5 \times 10^5$ cells/ml. The cultures are fed periodically, as needed, with medium and growth factor. The cultures are maintained for one to two weeks.

The cells in culture are harvested, washed, and resuspended in a physiologic buffer supplemented with autologous serum. Approximately $10^7$ to $10^9$ cells/kg are readministered to the patient one to three days following cytoreductive therapy.

The patients are further treated in vivo with an engraftment growth factor (50 $\mu g$/kg/day SF and 25 $\mu g$/kg/day PIXY321) for 7 to 21 days beginning two days following readministration of expanded progenitor cells (cellular preparation).

I claim:

1. A method for autologous hematopoietic cell transplantation in a patient receiving cytoreductive therapy, comprising:
   a. removing hematopoietic progenitor cells from the patient prior to cytoreductive therapy;
   b. expanding the hematopoietic progenitor cells ex vivo with
      (1) a growth factor comprising granulocyte macrophage-colony stimulating factor (GM-CSF) combined with interleukin-3 (IL-3), or a GM-CSF/IL-3 fusion protein, and
      (2) one or more growth factors selected from the group consisting of steel factor (SF), interleukin-1 (IL-1) and granulocyte-colony stimulating factor (G-CSF) and combinations thereof, to provide a cellular preparation comprising an expanded population of hematopoietic progenitor cells; and c. administering the cellular preparation to the patient following cytoreductive therapy.

2. The method of claim 1 wherein the growth factor comprises a GM-CSF/IL-3 fusion protein.

3. The method of claim 1 wherein the growth factor comprises SF and a Leu$^{23}$ Asp$^{27}$ Glu$^{34}$ hGM-CSF/Gly$_4$ Ser Gly$_5$ Ser/Pro$^8$ Asp$^{15}$ Asp$^{70}$ hIL-3 fusion protein.

4. The method of claim 1 wherein the ex vivo growth factor comprises IL-1α and Leu$^{23}$ Asp$^{27}$ Glu$^{34}$ hGM-CSF/Gly$_4$ Ser Gly$_5$ Ser/Pro$^8$ Asp$^{15}$ Asp$^{70}$ hIL-3 fusion protein, or a combination of SF, IL-1α and Leu$^{23}$ Asp$^{27}$ Glu$^{34}$ hGM-CSF/Gly$_4$ Ser Gly$_5$ Ser/Pro$^8$ Asp$^{15}$ Asp$^{70}$ hIL-3 fusion protein.

5. The method of claim 1 wherein the hematopoietic progenitor cell are obtained from peripheral blood.

6. The method of claim 1 wherein the hematopoietic progenitor cells are obtained from bone marrow.

7. The method of claim 1 further comprising the step of subsequently treating the patient in vivo with an engraftment growth factor for 3 to 21 days following administrating the cellular preparation to the patient, wherein the engraftment growth factor is selected from the group consisting of GM-CSF, IL-3, SF, GM-CSF/IL-3 fusion proteins and combinations thereof.

8. The method of claim 7 wherein the engraftment growth factor comprises SF and a GM-CSF/IL-3 fusion protein.

9. The method of claim 1 further comprising the step of pre-treating the patient with a recruitment growth factor in vivo for 1-7 days prior to removing hematopoietic progenitor cells, wherein the recruitment growth factor is selected from the group consisting of GM-CSF, IL-3, SF, GM-CSF/IL-3 fusion proteins and combinations thereof.

10. The method of claim 9, wherein the ex vivo growth factor and the in vivo recruitment growth factor comprise a GM-CSF/IL-3 fusion protein.

11. The method of claim 9, wherein the ex vivo growth factor comprises SF and Leu$^{23}$ Asp$^{27}$ Glu$^{34}$ hGM-CSF/Gly$_4$ Ser Gly$_5$ Ser/Pro$^8$ Asp$^{15}$ Asp$^{70}$ hIL-3 fusion protein.

12. The method of claim 9 wherein the ex vivo growth factor comprises IL-1α and Leu$^{23}$ Asp$^{27}$ Glu$^{34}$ hGM-CSF/Gly$_4$ Ser Gly$_5$ Ser/Pro$^8$ Asp$^{15}$ Asp$^{70}$ hIL-3 fusion protein, or a combination of SF, IL-1α and Leu$^{23}$ Asp$^{27}$ Glu$^{34}$ hGM-CSF/Gly$_4$ Ser Gly$_5$ Ser/Pro$^8$ Asp$^{15}$ Asp$^{70}$ hIL-3 fusion protein.

13. The method of claim 9 wherein the in vivo recruitment growth factor comprises SF and GM-CSF.

14. The method of claim 9 wherein the hematopoietic progenitor cells are obtained from peripheral blood.

15. The method of claim 9 wherein the hematopoietic progenitor cells are obtained from bone marrow.

16. The method of claim 9 further comprising the step of subsequently treating the patient in vivo with an engraftment growth factor for 3 to 21 days following administrating the cellular preparation to the patient, wherein the engraftment growth factor is selected from the group consisting of GM-CSF, IL-3, SF, GM-CSF/IL-3 fusion proteins and combinations thereof.

17. The method of claim 16 wherein the engraftment growth factor comprises SF and a GM-CSF/IL-3 fusion protein.

* * * * *

UNITED STATES PATENT AND TRADEMARK OFFICE
CERTIFICATE OF CORRECTION

PATENT NO. : 5,199,942

DATED : April 6, 1993

INVENTOR(S) : Steven Gillis

It is certified that error appears in the above-identified patent and that said Letters Patent is hereby corrected as shown below:

Title page, item [57]
IN THE ABSTRACT:

Line 14, please delete [follwoing] and replace with -- following --.
Line 15, please delete [comprising] and replace with -- comprises --.

Column 2, line 17, delete [suppresion] and replace with -- suppression --.
Column 4, line 67, delete [protein] and replace with -- proteins --.

Signed and Sealed this

Twenty-second Day of February, 1994

*Attest:*

BRUCE LEHMAN

*Attesting Officer*     *Commissioner of Patents and Trademarks*

Adverse Decisions In Interference

Patent No. 5,199,942, Steven Gillis, METHOD FOR IMPROVING AUTOLOGOUS TRANSPLANTATION, Interference No. 103,853, final judgment adverse to the patentee rendered September 3, 1998, as to claims 1-3.

*(Official Gazette October 27, 1998)*